United States Patent
Ozkul et al.

(10) Patent No.: US 8,532,780 B2
(45) Date of Patent: Sep. 10, 2013

(54) SURGICAL IMPLANT FOR ELECTRONIC ACTIVATION OF DYSFUNCTIONAL EUSTACHIAN TUBE

(76) Inventors: Tarik Ozkul, Sharjah (AE); Murat Haluk Ozkul, Kadikoy (TR)

( * ) Notice: Subject to any disclaimer, the term of this patent is extended or adjusted under 35 U.S.C. 154(b) by 0 days.

(21) Appl. No.: 13/575,654

(22) PCT Filed: Jan. 11, 2010

(86) PCT No.: PCT/IB2010/050077
§ 371 (c)(1),
(2), (4) Date: Jul. 27, 2012

(87) PCT Pub. No.: WO2011/083370
PCT Pub. Date: Jul. 14, 2011

(65) Prior Publication Data
US 2012/0296393 A1  Nov. 22, 2012

(51) Int. Cl.
*A61N 1/05* (2006.01)
(52) U.S. Cl.
USPC .......................................................... 607/48
(58) Field of Classification Search
USPC ................................................... 607/48
See application file for complete search history.

(56) References Cited

U.S. PATENT DOCUMENTS

| 7,277,749 B2 * | 10/2007 | Gordon et al. ..................... 607/2 |
| 2002/0077674 A1 * | 6/2002 | Strome et al. ................... 607/61 |
| 2003/0208250 A1 | 11/2003 | Edwards et al. |
| 2008/0275513 A1 | 11/2008 | Lattner et al. |

FOREIGN PATENT DOCUMENTS
WO 2009/037689 A2 3/2009

OTHER PUBLICATIONS

Cantekin, E et al., "Dilation of the Eustachian tube by electrical stimulation of the mandibular nerve." Ann. Otol. Rhino. I. Laryngol., 88: 40-51, 1979.
Honjo, I. et al., "Experimental study of Eustachian tube by electrical stimulation of the manibular nerve". Ann. Otol. Rhino I. Laryngol., 88: 40-51, 1979.
International Preliminary Report on Patentability for International Application No. PCT/IB2010/050077, dated Apr. 30, 2012.
International Search Report for International Application No. PCT/IB2010/050077, dated Apr. 21, 2010.
Written Opinion of the International Searching Authority for International Application No. PCT/IB2010/050077, dated Apr. 21, 2010.

* cited by examiner

*Primary Examiner* — George Manuel
(74) *Attorney, Agent, or Firm* — Cantor Colburn LLP

(57) ABSTRACT

This invention comprises a totally implantable Eustachian tube activation device which is intended for patients suffering from Eustachian Tube Dysfunction ailment. The device electrically stimulates the muscles activating the Eustachian tube to perform the opening maneuver of the Eustachian tube valve to aerate the middle ear cavity. The unit is hermetically sealed in a suitable biocompatible container and implanted in a suitable location in close proximity to Eustachian tube. The frequency of the stimulation of the implant may be fixed or can be altered depending on the condition of the patient.

18 Claims, 5 Drawing Sheets

SURGICAL IMPLANT FOR ELECTRONIC ACTIVATION OF DYSFUNCTIONAL EUSTACHIAN TUBE

FIELD

The present invention relates to category of surgical instruments devices or methods for transferring non-mechanical form of energy to the body. More specifically, the present invention relates to sub-category of "arrangements in connection with implantation of stimulators". The apparatus is designed to stimulate muscles controlling the Eustachian Tube electrically and intended to be implanted in humans and animals suffering from medical condition of "Eustachian Tube Dysfunction" or related ailments.

BACKGROUND

The Eustachian tube is a hollow tube that originates in the back of the nose and connects the nasal cavity to the middle ear space. The middle ear space is the hollowed out portion of the skull bone that contains the hearing mechanism, which is covered by eardrum on one side and cochlea on the other side. The Eustachian Tube provides ventilation, drainage and protection of mid ear against reflux, microorganisms, excessive sound pressure and pressure changes in pharynx. In adults, the Eustachian tube is approximately 35 mm long and approximately 3 mm in diameter. The first part of the Eustachian tube is supported by cartilage and the last part that is close to the middle ear space is located inside the bone structure. The lining tissue of the Eustachian tube is similar to tissue that covers the nasal cavity and responds to external stimulants just as nasal tissue does.

The main function of the Eustachian tube is to provide ventilation to the middle ear space, ensuring that its pressure remains at slightly negative but close to ambient air pressure. Another function of the Eustachian tube is to drain secretions and debris from the middle ear space. Several small muscles located in the back of the throat and palate control the opening and closing action of the tube. Typical muscular actions like swallowing and yawning cause contractions of these muscles and activate Eustachian tube function time to time to achieve its pressure regulation function.

Eustachian tube is normally closed most of the time to prevent contaminants contained in the nasal cavity to reach the middle ear space cavity. Disorders of ET are basically either "dilatory" type (failure to open adequately) or "patulous" type (failure to maintain tube closed at rest). Dysfunction of an Eustachian tube makes the tube always open and this condition is called a "patulous" Eustachian tube. Patients with "patulous" dysfunctional Eustachian tube suffer from frequent, chronic ear infections. A more common form of the Eustachian tube dysfunction causes partial or complete blockage of the Eustachian tube which cause sensations of popping, clicking, and ear fullness as well as moderate to severe ear pain associated with the condition.

Many people suffer from Eustachian Tube (ET) dysfunction and this condition affects quality of their life. There have been many different attempts over the history to solve the problem of ET dysfunction. Most devices developed are in the form of tubes or similar inserts which are inserted into Eustachian tube to keep it open and provide ventilation. Patents and applications; WO 2009/001358, WO 2006/049131, US patent US 2009/0099573, WO 2005/082303, U.S. Pat. No. 4,015,607 can be cited in this category which more or less achieve the purpose using this method. U.S. Pat. No. 4,888,017 proposes a different approach by providing an inflatable gadget to open the Eustachian tube momentarily by patient applying pressure manually to activate the device which forces open the ET tube. Another remedy used by surgeons to rectify Eustachian tube dysfunction ailment is to fix a grommet on the eardrum of the patient to provide ventilation for the middle ear cavity. These methods mentioned above have some complications. Most patients report that insert devices used for keeping Eustachian tube open simply do not remain in place for long time and provide solution only for a limited time. Grommets (rings) placed on ear drums also tend to fall after several weeks. Additionally, keeping the ET tube always open solves one problem but causes secondary problems by providing an open path for liquid and external contaminants to flood the mid ear cavity.

Patents like WO 01/43653 and WO 2008/079476 provides alternative techniques of surgical manipulation of ET tube by laser and radio frequency techniques to remedy the problem of Eustachian Tube Dysfunction related complications. Overall, many humans as well as animals are afflicted with ET dysfunction problem.

The present invention attempts to solve the problem with a different mechanism which activates muscles of the ET. The muscles surrounding the ET tube activate the opening/closing action of the ET valve. As R. Leuwer writes in an article titled "Mechanics of Eustachian tube" published in "Chronic Otitis Media. Pathogenesis-Oriented Therapeutic Management", pp 129-134 edited by B. Ars (2008 Kugler Publications), Eustachian tube has a complex muscular compliance which involves influence of tensor veli palatine muscle, levator veli palatine muscle and medial pterygoid muscle. Most researchers agree that tensor veli palatini and levator veli palatine are primary activators of the Eustachian tube whereas medial pterygoid muscle has secondary influence on function of the ET by changing the position of the ET and the veli muscles mentioned above.

In 1979, Cantekin et. al reported in an article published in Ann Otol Rhinol Laryngol. 1979 January-February; 88(1 Pt 1):40-51 that they have conducted a series of experiments with Rhesus monkey and observed that Eustachian Tube (ET) tube action is initiated by muscles surrounding the ET tube. This, indeed has proven that Eustachian tube is not a simple tube and its function can be controlled by a series of coordinated activation of the surrounding muscles.

SUMMARY

The approach of the present invention is to fix the problem that underlies the Eustachian tube dysfunction problem by way of stimulating muscles through an electronic transplant by injecting current to the involved muscles or nerves controlling the muscles. Eustachian tube is not a simple tube that connects the nasal cavity to the middle ear cavity, it is actually a tubular valve which opens time to time to equalize the pressure inside the mid ear cavity. The ET tube is normally rests in closed state and only opens temporarily for a short time (about 1 sec.) to execute its function. The opening action of the ET tube is achieved by two muscles located on different sides of the ET tube. These two tubal muscles are the Levator Veli Palatini Muscle (LVPM) and the Tensor Veli Palatini muscle (TVPM). Among the two, Tensor Veli Palatini (TVPM) is the main tubal dilator which performs the Eustachian tube function. However LVPM and TVPM function together for a successful opening action of ET. Some researchers also claim that medial pterygoid muscle also plays a role indirectly by making affect of the palatini muscles more effective. Coordinated action of these muscles is necessary for successful opening and closing of the Eustachian Tube which results in aeration and pressure equalization of the mid ear cavity.

The present invention is contemplated as a self contained unit with electrodes, power source, electronics and microcontroller in a suitable package to be transplanted in a suitable location in close proximity to the Levator Veli Palatini (LVPM) and the Tensor Veli Palatini muscles (TVPM) of the Eustachian Tube. Microcontroller and the associated electronics of the present invention send an orchestrated series of pulses to the said muscles through electrodes to achieve the desired action of the ET tube.

Normally in healthy subjects, the ET aeration action is done time to time through actions like yawning and swallowing. The present invention is contemplated to have different scenarios with different frequencies of muscular stimulation to be selected by the ENT specialist depending on the condition of the patient. An external adjustment unit with wireless connectivity is contemplated to be used for selecting suitable scenario, important parameters and relaying this information to the implanted unit wirelessly.

In healthy subjects, the pressure inside the inner ear is maintained slightly negative than the ambient pressure through the action of Eustachian tube. The present invention is contemplated to achieve the same through activation of the ET tube from time to time. How frequent this action needs to be done may depend on the individual patient and may be different for different patients. To achieve this adaptability, the present invention accommodates sensor inputs as well as adaptable frequency plans. In one embodiment, a suitable pressure sensor may be used to sense the inner ear pressure and activate the stimulation action when the pressure is above or below certain limits. In another embodiment, a tilt sensor may be used to initiate stimulation sequence as the patient tilts his or her head. Yet in another embodiment, the stimulation action can be purely time based and do not depend on sensor inputs. As an example of time based activation, the stimulation action can be repeated once every 2 minutes. The present invention is designed to be activated by different scenarios to find the best fit for the patient.

The invention makes it possible to use variety of different sensors for triggering the stimulation action of the muscles and designed to work with or without sensors. Different types of sensors that can be used toward this goal are already known by the people who are skilled in the state of the art. Operation of the invention without any sensors is also possible through strictly time-based activation.

The device is a battery-operated one, which may be equipped with long life or rechargeable type batteries. Battery operated implant technology is already very well known by those who are skilled in the state of art and the invention uses the known techniques for embedding, recharging and housing the unit in a biocompatible hermetically sealed container. Charging of batteries can be done through a coil suitable placed under skin. By inductively coupling the coil with an external RF field the batteries can be charged. This technology of charging is being used by many other implants like implant US 2008/0147144 and technology is well known by those who are skilled in this art.

The electronics contained in the invention comprises, power circuit, microcontroller, communication unit and signal conditioning unit. Microcontroller executes the program, communicates with the external world, read sensor inputs and generates output signal to activate the ET muscles. There are vast amount of choices for embedded processors with low power consumption and high processing power thanks to increasing amount of mobile smart devices surround us. One such embodiment of the invention may contain commercially available ARM series processors as the choice for the microcontroller.

Signal conditioner converts voltage signals to current signals necessary to activate the muscles or the nerves controlling the muscles. Design of signal conditioning circuits for muscle activation is well know by those skilled in the art of electronics design. One such design is published by E. Bruun and E. U. Haxthausen in Electronics Letter, in November 1991, vol. 27, pp. 2172-2174, titled "Current conveyor based EMG amplifier with shutdown control".

External communication of the implant with the external world is provided through a digital communication link. There are excellent low-power consuming chipsets and protocols based on emerging digital standards. ZigBee is such a technology based on IEEE 802.15.4-2003 which is suitable toward this purpose. Another possible choice is Bluetooth technology which can also be used toward the purpose of establishing communication between implant and the external world. These communication technologies are well known by those who are skilled in the art of electronics and computer engineering. One such embodiment of the invention may use ZigBee chipset for communication with the external world. Another embodiment of the invention may use Bluetooth as the selected standard to communicate with the external world which opens the possibility of using Bluetooth equipped mobile phones or computers to be used for communicating with the implant unit. Current state of the art in electronics offers the possibility of integrating most electronics on a single Field Programmable Gate Array (FPGA) chip. One embodiment of the invention may use a single FPGA to integrate microcontroller, Zigbee and signal conditioning on a single FPGA chip. These technologies are well known to those skilled in this art of FPGA design.

The signal generated by the implant is delivered to the muscles or muscle nerves through commercially available medical grade wires and electrodes. One such embodiment of the invention may use Teflon coated stainless steel (SS) wire (316LVM, Cooner Wire Co.) or 90% platinum-10% iridium (Wr) wire (Medwire, Sigmund Cohn Corp.) and commercially available implantable electrodes like one in EP 0 408 358. Another embodiment of the invention may use intramuscular electrode made from 7-strain stainless steel insulated by a biocompatible material for fabrication of a suitable electrode. The electrodes that can be used for muscle activation can be intramuscular type which can be implanted inside the muscle, or epymysial type which can be placed on the muscle, or cuff electrode which can be placed over the nerve stem of the muscle, or it can be intraneural electrode which can be placed inside the nerve stem of the muscle. The materials and the techniques are well known by those who are skilled in the art. One possible source for this information is "Neuroprosthetics, Theory and practice" book which is published by World Scientific publishing in 2004 which is edited by Kenneth W. Horch and Gupreet S. Dhillon which is an authoritative book on the subject.

The present invention is intended to be placed subcutaneously in close proximity of the Eustachian tube muscles. One possible location is the temporal bone location favored for Cochlear implants or implantable hearing aids. The location and the practice is well known by the surgeons skilled in the art of such procedures. One possible source to this information is a book titled "Cochlear implants" which is published in 2006 by Thieme Medical Publishers.

DESCRIPTION

Figure 1:
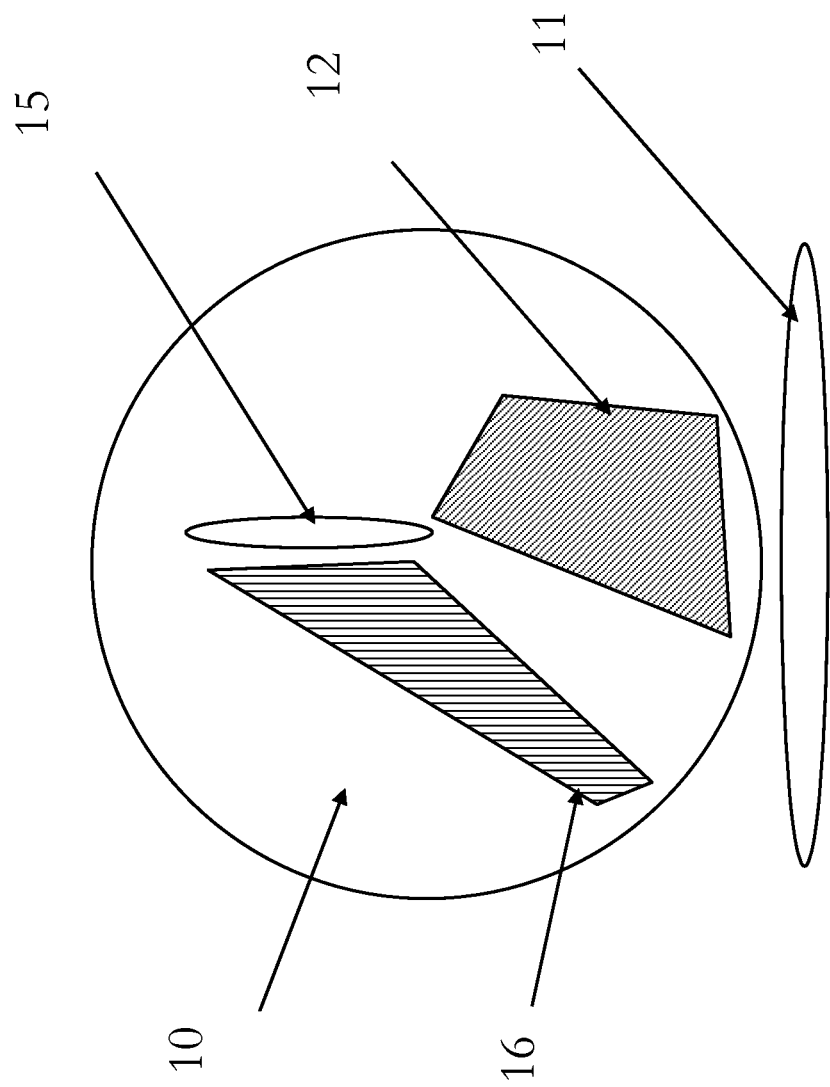
FIG. 1. Location of ET, TVP and LVP muscles with respect endoscopic view of the Eustachian tube in relaxed state where the ET tube is closed.

The operation of the present invasion invention will now be described with the aid of figures. The invention is intended to electrically stimulate muscles that operate Eustachian tube. Eustachian tube connects nasal cavity to middle ear cavity to provide pressure equalization and protection. Eustachian tube is not a simple pipe but a complex valve actuated by several muscles around it. FIG. 1 shows the endoscopic view 10 of Eustachian tube in its normally closed state. When the actuator muscles, tensor veli palatini muscle 16, levator veli palatine muscle 12 and medial pterygoid muscle 11 are in relaxed state, the opening of Eustachian tube 15 is closed and no air exchange between the two cavities takes place.

Figure 2:
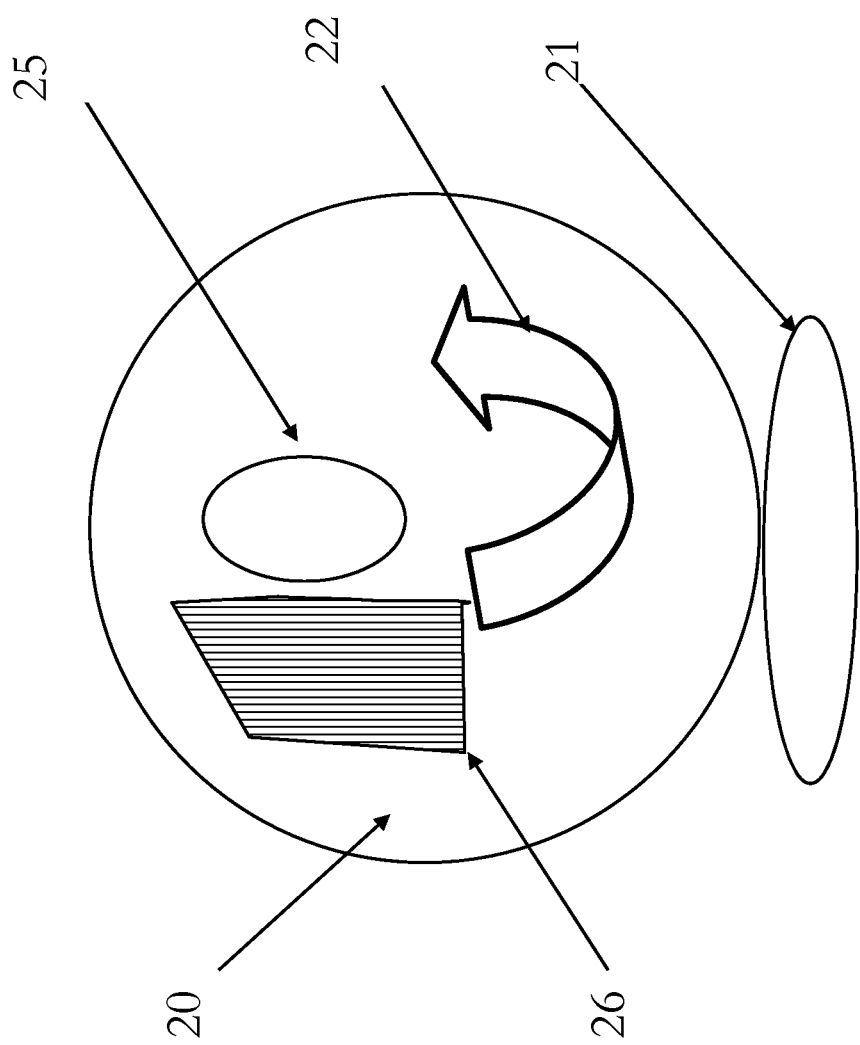
FIG. 2. Location of ET, TVP and LVP muscles with respect endoscopic view of the Eustachian tube in muscles contracted state where the ET tube is open.

FIG. 2 shows endoscopic view 20 of Eustachian tube with its actuator muscles in activated state. Medial pterygoid muscle 21 contracts and modifies the location of the Eustachian tube, levator veli palatini muscle 22 contracts and rotates the Eustachian tube and finally the tensor veli palatini 26 contracts and opens the opening of the Eustachian tube 25.

Figure 3:
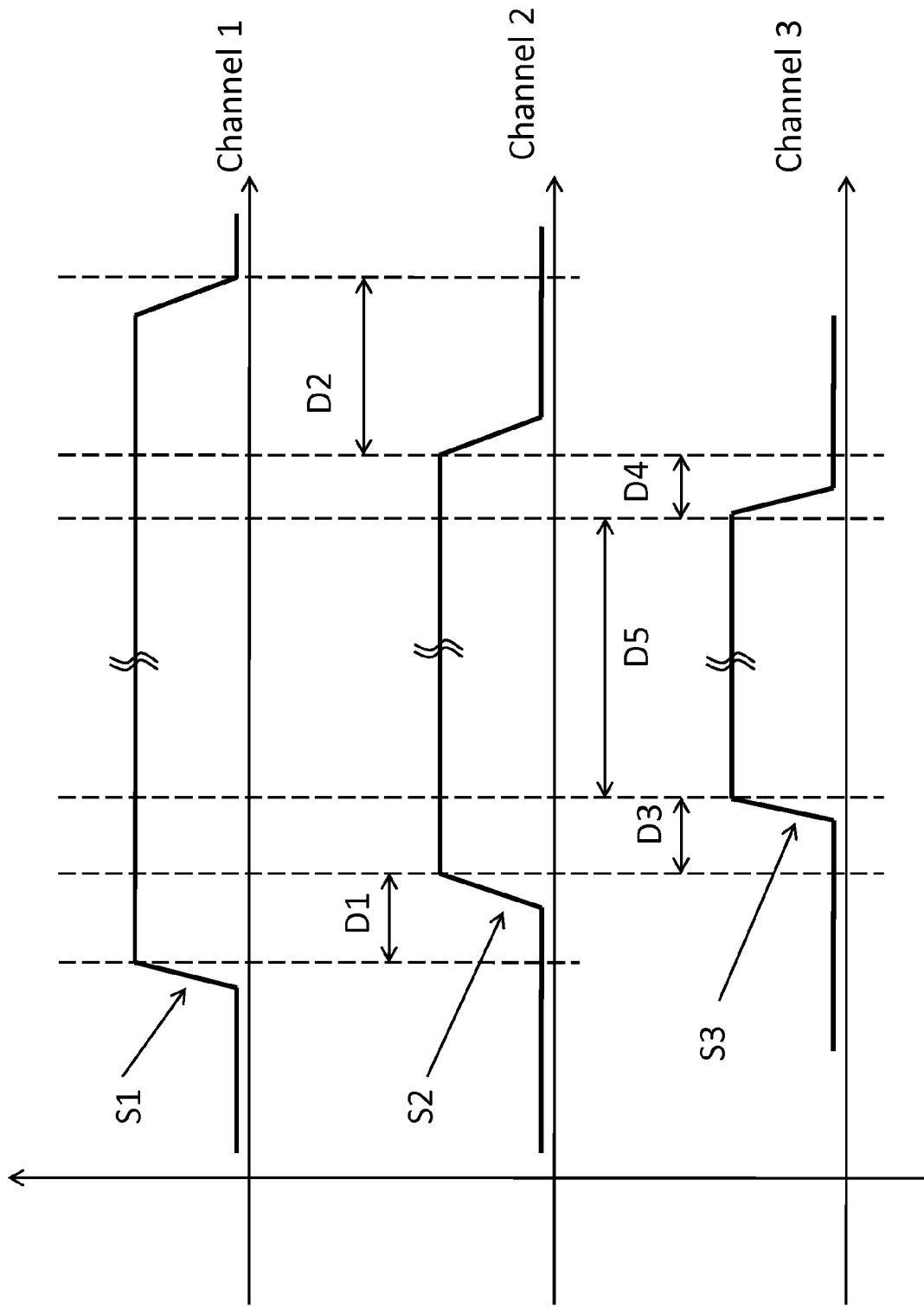
FIG. 3. The shape of pulses for different muscle groups of Eustachian Tube.

The contractions of these muscles occur in a particular sequence for efficient opening of Eustachian tube. The sequence of muscle activation is shown in FIG. 3. Medial pterygoid muscle activity is shown in Channel 1 as waveform S1. S1 at low level indicates relaxed muscle state 11 and S1 at high level indicates contracted muscle state 21. Channel 2 indicates activity of levator veli palatini muscle. S2 waveform at high level indicates contracted levator veli palatine muscle state 22. S2 at low level indicates relaxed levator veli palatine muscle state 12. Channel 3 indicates activity of tensor veli palatini muscle. Waveform S3 indicates actuation of tensor veli palatine muscle. S3 at high level means contracted tensor veli palatine muscle 26 and S3 at low level means tensor veli palatine in relaxed state 16. The Eustachian tube opening activity starts with medial pterygoid muscle (S1) contracting first. After a delay time of D1, the levator veli palatini (S2) contracts. After a delay time of D3, the tensor veli palatine (S3) contracts and opens the Eustachian tube. During this instant, the ET tube is open and middle ear cavity is aerated. The open state of the Eustachian tube lasts for D5 amount of time. After expiration of D5, the tensor veli palatine (S3) relaxes which is followed by relaxation of the levator veli palatine muscle (S2) after a delay time of D4. Finally, after a delay time of D2, the medial pterygoid muscle (S1) relaxes and Eustachian tube returns to its normally closed state.

Figure 4:
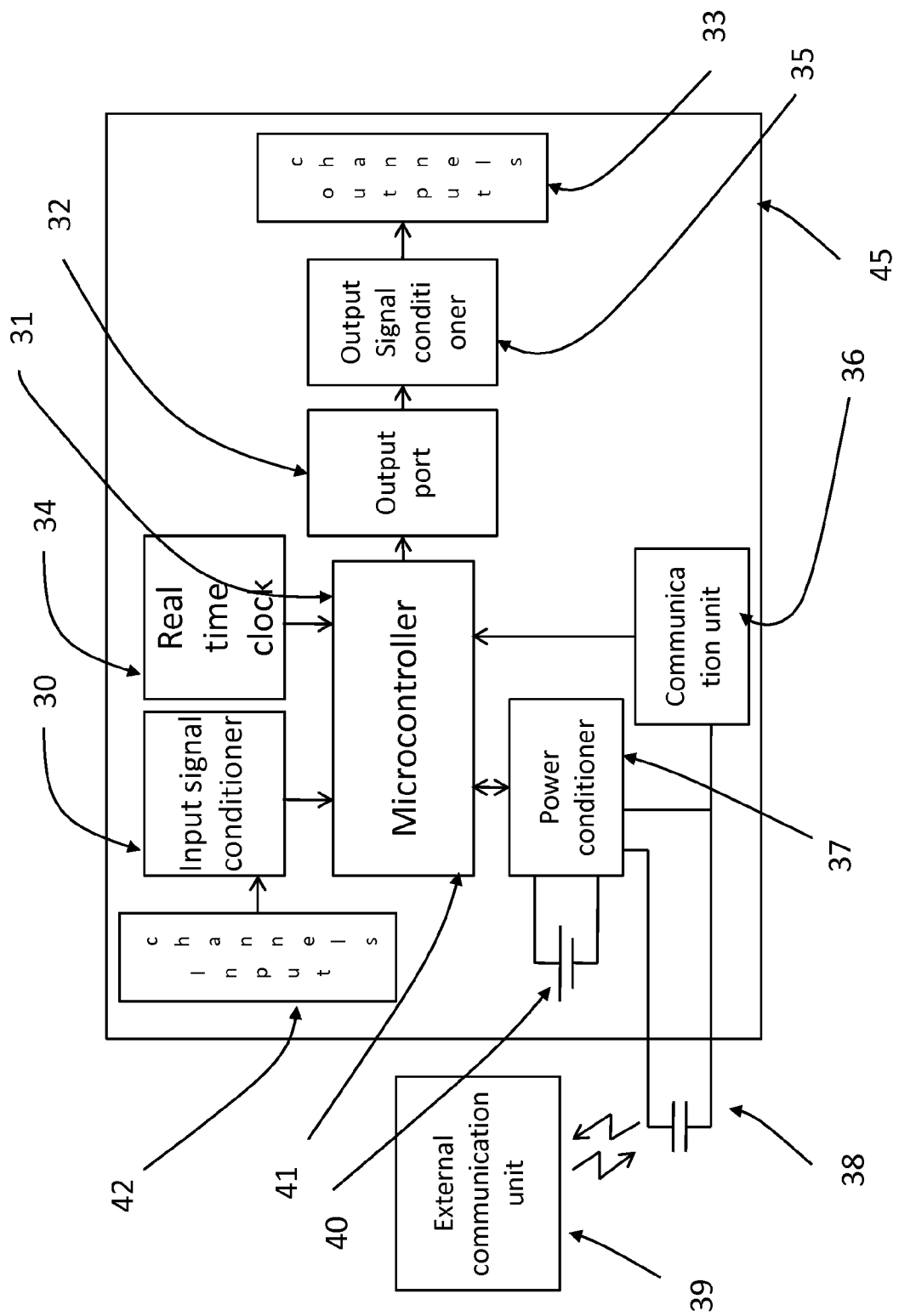
FIG. 4. Block diagram of the system of the implant.

The present invention is designed to activate muscles in this particular sequence. The block diagram of the invention is shown in FIG. 4. The electrodes for stimulating muscles are connected to output channels 33. Output signal conditioner 35 is responsible for generating voltage to current conversion and adjusting amplitude and frequency of the signals that are send to electrodes. Microcontroller 31 is the main processor of the implant and responsible for generating pulse sequences, delay times and deciding when to send the pulse sequences to electrodes. Microcontroller 31, does this by executing a program embedded in its memory. Waveforms similar to S1, S2, S3 shown in FIG. 3 are sent to electrodes connected individually to output channels 33 to ensure proper sequence of muscle contraction for successful activation of Eustachian tube. Decision about when to send waveforms S1, S2, S3 to electrodes is done by microcontroller 31, either by timing between pulse sequences or by depending on the sensor inputs or by external triggers. As an example to decision by timing, a particular embodiment of invention may send sequence of pulses to open Eustachian tube every 1500 seconds. A real-time clock 34 connected to microcontroller 31 helps to determine delay times as well as different application schedules dependent on time of the day. As an example, a particular embodiment of the invention may apply pulse sequences less frequently at nighttime then daytime. Decision about when to send pulse sequences to electrodes can also be done by sensor inputs. Sensors are connected to input channel 42 and input signals are conditioned by input signal conditioner 30. A particular embodiment of the invention may use a pressure sensor to detect the pressure inside the middle ear cavity and whenever the pressure exceeds certain threshold level, the microcontroller 31 decides to send pulse sequences to open Eustachian tube. Another particular embodiment of the invention may use tilt sensor to sense the position of the head and decide to activate the Eustachian tube muscles whenever patient bows his/her head. Yet another particular embodiment of the invention may use an electrode connected to a particular muscle to receive the trigger signal. As an example, whenever patient performs a swallow action, an electrode implanted in one of the suitable muscles or nerves involved in swallow action can provide the input signal to initiate the actuation of the Eustachian tube. In this case, the electrode that comes from the muscle or the nerve becomes the input sensor connected to input channel 42. Yet another way of activation can be through the signal provided by the external communication unit 39. External communication unit 39, is an external device which can be used to communicate with the implant 45 through digital or analog communication techniques. External communication unit 39 can be a PDA (personal digital assistant), a smart phone or any device capable of using low-power digital communication standards like ZigBee, Bluetooth, infrared or like. The device 39 can be used to configure the parameters of the program running inside microcontroller 31 as well as sending a signal to trigger the action to initiate Eustachian tube actuation pulse sequence. The communication unit 36 inside the implant uses the antenna 38 to receive the signals from the external communication unit 39. The communication between external communication unit 39 and internal communication unit 36 is bidirectional. As a result, the external communication unit 39 can also be used for diagnosing, interrogating the implant 45. As an example, one particular embodiment of the invention may use external communication unit 39 to show the power remaining in its batteries. Power conditioner 37 monitors the power in battery 40, which supplies power to the implant 45. The battery 40 can be charged through a coil 38, which is made up of few turns of medical grade wire placed subcutaneously under the skin of the patient.

Figure 5:
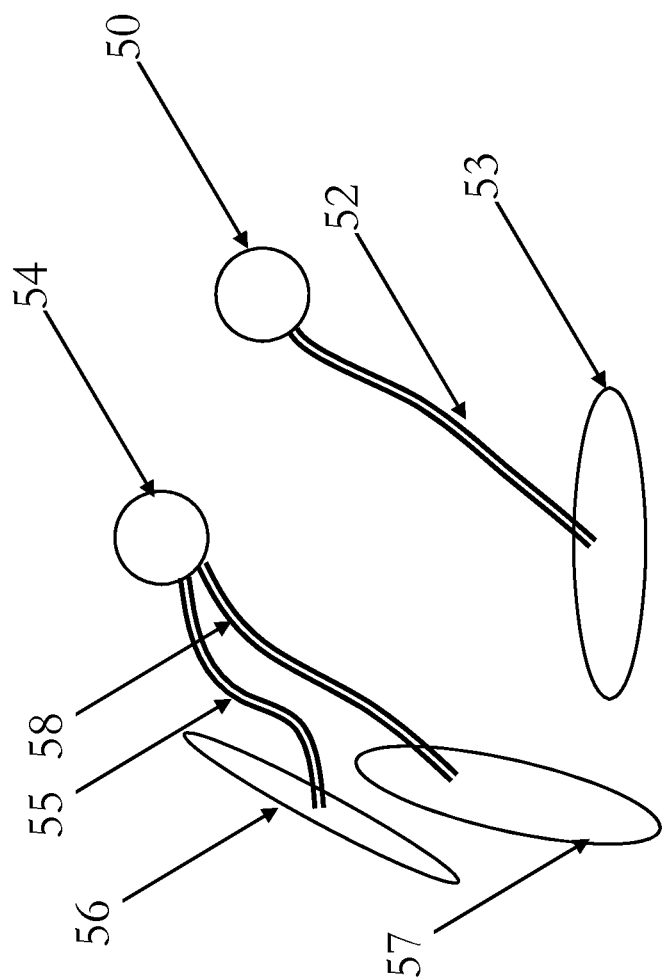
FIG. 5. Nerves, muscles and ganglions involved in Eustachian tube activation.

The activation of the muscles is done using electrodes connected to output channels 33 of implant 45 shown in FIG. 4. The connection mechanism to muscles will be described with the aid of FIG. 5. FIG. 5 shows the muscles, the nerves and the ganglions involved in activation of Eustachian tube. Sphenopalatine ganglion 50 is where the nerve stem 52 to levator veli palatini muscle 53 originates. Otic ganglion 54 on the other hand generates the nerve stem 55 for tensor veli palatini muscle, which eventually reaches tensor veli palatini muscle 56. The nerve stem 58 for medial pterygoid muscle also starts from otic ganglion 54 and eventually reaches medial pterygoid muscle 57. In one embodiment, activation of these muscles can be done using intramuscular electrodes placed inside muscles 56, 57 and 53. In another embodiment, these muscles can be activated through epymysial (surface) electrodes stapled on the muscles 56, 57 and 53. Yet in another embodiment, the muscles 53, 56 and 57 can be activated through cuff electrodes attached to nerve stems 52, 55, 58. Yet in another embodiment, the muscles 53, 56 and 57 can be activated through intraneural electrodes placed inside nerve stems 52, 55 and 58. The exact selection of the type of electrode for the particular patient needs to be done by a competent neurosurgeon experienced in the art of electrode placement. The type of electrodes to be used for activation of muscles is well known in the state of the art and the electrodes can be manufactured using medical grade wires or purchased commercially. One possible source for this information is "Neuroprosthetics, Theory and practice" book which is published by World Scientific publishing in 2004 which is edited by Kenneth W. Horch and Gupreet S. Dhillon which is an authoritative book on the subject.

The present invention is intended to be placed subcutaneously in close proximity of the Eustachian tube muscles. One possible location is the temporal bone location favored for Cochlear implants or implantable hearing aids. The location and the practice is well known by the surgeons skilled in the art of such procedures. One possible source to this information is a book titled "Cochlear implants" which is published in 2006 by Thieme Medical Publishers.

The invention claimed is:

1. A method for use with two or more Eustachian tube related muscles, the two or more Eustachian tube related muscles comprising a tensor veli palatini muscle, a levator veli palatini muscle, and a medial pterygoid muscle, for the treatment of Eustachian tube dysfunction, the method comprising:
applying a programmed series of stimulation pulses simultaneously to the two or more Eustachian tube related muscles through implanted electrodes to activate the two or more Eustachian tube related muscles; and
repeating application of said series of stimulation pulses at certain intervals to the implanted electrodes to perform activation of the Eustachian tube.

2. The method as set forth in claim 1, wherein said series of stimulation pulses applied to the muscles may be different for each implanted electrode.

3. The method as set forth in claim 2, wherein said series of stimulation pulses applied to the muscles is adjustable and can be changed.

4. The method as set forth in claim 1, wherein said certain intervals of said series of stimulation pulses may be determined based on time delay basis, or by sensor inputs, or by trigger signal provided by external means, or by a combination of these methods thereof.

5. The method as set forth in claim 4, wherein said certain intervals of said series of stimulation pulses are based on time delay basis, the said time delay is adjustable.

6. The method as set forth in claim 4, wherein said certain intervals of said series of stimulation pulses are determined by sensor inputs, the said sensor inputs come from sensors located inside or outside the body of the patient.

7. The method as set forth in claim 4, wherein said certain intervals of said series of stimulation pulses are determined based on trigger signal coming from an external unit outside the body of the patient.

8. The method as set forth in claim 1, wherein the implanted electrodes can be one or more electrodes placed in or on the muscles or nerve stems of the muscles.

9. A system for use with one or more Eustachian tube related muscles of a patient for the treatment of Eustachian Tube Dysfunction ailment, the system comprising:
an implant comprising:
an electrode assembly adapted to be implanted in the patient to stimulate one or more Eustachian tube related muscles, and
an output signal conditioner in communication with the electrode assembly which generates a pulse sequence for the electrode assembly,
an output channels unit connecting the electrode assembly to the output signal conditioner unit,
an input signal conditioner which receives a signal from multiple sensors connected to input channels,
a processing element in communication with the output signal conditioner and the input signal conditioner, wherein the processing element executes a program and generates output signals,
a power unit with batteries supplying power to the electrode assembly, wherein the power unit monitors power level of the batteries and charges the batteries,
a communication unit communicating with the processing element, and
an internal real-time clock connected to the processing element;
and
an external communication unit communicating with the communication unit of the implant.

10. The system according to claim 9,
wherein the electrode assembly comprises one or more electrodes adapted to be implanted in the one or more Eustachian tube related muscles or nerves leading to muscles, wherein the one or more electrodes is selected from an intramuscular electrode, an epymysial electrode, a cuff electrode, an intraneural electrode, or a combination of the foregoing electrodes, and
wherein each electrode of the electrode assembly is connected to a separate channel of the output channels unit.

11. The system according to claim 9,
wherein the output signal conditioner converts output signals generated by the processing element to a pulse sequence and adjusts amplitude, frequency, waveform and duration of the pulse sequence and sends the pulse sequence to electrodes of the electrode assembly through said output channels unit.

12. The system according to claim 11 wherein the current pulse sequence sent from said output channels unit may be different for each electrode of the electrode assembly.

13. The system according to claim 9
wherein the input signal conditioner receive signals from one or more sensors connected to said input channels.

14. The system according to claim 9
wherein the system is capable of operation with or without said sensors.

15. The system according to claim 9
wherein the processing element generates output signals based on input from said multiple sensors, from time delay calculations done internally by the processing element, from a trigger signal supplied by the external communication unit-, or from a combination of these methods.

16. The system according to claim 9
wherein the communication unit is capable of communicating with the external communication unit bi-directionally using digital wireless or digital infrared communication techniques through said external communication unit.

17. The system according to claim 9 wherein the external communication unit executes an internal program to convert the preference of a user into appropriate digital parameters and communicates these parameters to the communication unit of the implant.

18. A system according to claim 9 wherein the external independent communication unit is capable of displaying diagnostic information sent from said communication unit of the implant.

\* \* \* \* \*

UNITED STATES PATENT AND TRADEMARK OFFICE
CERTIFICATE OF CORRECTION

Page 1 of 1

PATENT NO. : 8,532,780 B2
APPLICATION NO. : 13/575654
DATED : September 10, 2013
INVENTOR(S) : Tarik Ozkul and Murat Haluk Ozkul It is certified that error appears in the above-identified patent and that said Letters Patent is hereby corrected as shown below:

On the Title Page, item (76),
This patent currently names "Tarik Ozkul, Sharjuh, (AE)" as inventor. Pursuant to a Request to Correct Inventorship filed with the United States Patent and Trademark Office on June 2, 2014, the residence of "Sharjuh, (AE)" for inventor Tarik Ozkul should be deleted and replaced with the "Istanbul, (TR)."

Signed and Sealed this
Fifth Day of August, 2014

Michelle K. Lee
*Deputy Director of the United States Patent and Trademark Office*